US012616416B2

(12) United States Patent
Du et al.

(10) Patent No.: US 12,616,416 B2
(45) Date of Patent: May 5, 2026

(54) SYSTEM OF MONITORING FOETAL GROWTH, METHODS OF MONITORING AND FORMING THE SYSTEM

(71) Applicants: Agency for Science, Technology and Research, Singapore (SG); National University Hospital (Singapore) Pte Ltd, Singapore (SG)

(72) Inventors: Yao Du, Singapore (SG); Mahesh Choolani, Singapore (SG); Jun Hui Ho, Singapore (SG); Renzhe Bi, Singapore (SG); Poongkulali Rajarahm, Singapore (SG); Malini Olivo, Singapore (SG)

(73) Assignees: Agency for Science, Technology and Research, Singapore (SG); National University Hospital (Singapore) Pte Ltd, Singapore (SG)

( * ) Notice: Subject to any disclaimer, the term of this patent is extended or adjusted under 35 U.S.C. 154(b) by 817 days.

(21) Appl. No.: 17/927,853

(22) PCT Filed: May 31, 2021

(86) PCT No.: PCT/SG2021/050305
§ 371 (c)(1),
(2) Date: Nov. 25, 2022

(87) PCT Pub. No.: WO2021/246959
PCT Pub. Date: Dec. 9, 2021

(65) Prior Publication Data
US 2023/0200721 A1 Jun. 29, 2023

(30) Foreign Application Priority Data
Jun. 3, 2020 (SG) .......................... 10202005227W

(51) Int. Cl.
A61B 5/00 (2006.01)
A61B 5/107 (2006.01)
A61B 5/11 (2006.01)

(52) U.S. Cl.
CPC .......... *A61B 5/4362* (2013.01); *A61B 5/0077* (2013.01); *A61B 5/1072* (2013.01); *A61B 5/11* (2013.01)

(58) Field of Classification Search
CPC ... A61B 5/4362; A61B 5/0077; A61B 5/1072; A61B 5/11
See application file for complete search history.

(56) References Cited

U.S. PATENT DOCUMENTS 6,575,757 B1 6/2003 Leight et al.
9,121,048 B1 * 9/2015 Blanco ................... C12Q 1/025
(Continued)

FOREIGN PATENT DOCUMENTS

CN 203776906 U 8/2014
CN 110680655 A 1/2020
(Continued)

OTHER PUBLICATIONS

Morse et al., "Fetal Growth Screening by Fundal Height Measurement," Best Practice & Research Clinical Obstetrics and Gynaecology, vol. 23, 2009, pp. 809-818.
(Continued)

*Primary Examiner* — May A Abouelela
(74) *Attorney, Agent, or Firm* — Shackelford, McKinley & Norton, LLP

(57) ABSTRACT
A system for monitoring foetal growth. The system may include a plurality of devices. Each device of the plurality of devices may be configured to determine measurements of a baby bump over a time period, and may be further configured to store the measurements. The system may also
(Continued)

include a server configured to receive the measurements from each of the plurality of devices. The server may be configured to compare the measurements from different devices of the plurality of devices. The system may be further configured to send an alert upon detecting an abnormality based on the measurements from the different devices of the plurality of devices.

20 Claims, 11 Drawing Sheets

(56)                    References Cited

U.S. PATENT DOCUMENTS

| | | | |
|---|---|---|---|
| 2010/0088915 A1 | 4/2010 | Neff | |
| 2010/0186101 A1* | 7/2010 | Nie | C07K 16/40 |
| | | | 800/9 |
| 2010/0274145 A1 | 10/2010 | Tupin, Jr. et al. | |
| 2014/0037686 A1* | 2/2014 | Mercenier | A23L 33/135 |
| | | | 424/234.1 |
| 2016/0310062 A1 | 10/2016 | Larson | |
| 2016/0367214 A1* | 12/2016 | Myklebust | A61B 5/02438 |
| 2017/0000181 A1* | 1/2017 | Erdmann | A23L 33/30 |
| 2019/0216366 A1* | 7/2019 | Hall | A61B 5/1128 |
| 2019/0365263 A1* | 12/2019 | Raj | A61B 5/0024 |
| 2020/0063204 A1* | 2/2020 | Bisgaard | G01N 33/92 |
| 2021/0023195 A1* | 1/2021 | Empey | C07K 14/005 |
| 2021/0318871 A1* | 10/2021 | Kale | G16H 50/20 |
| 2022/0208386 A1* | 6/2022 | Adams | G01N 33/6896 |
| 2022/0257695 A1* | 8/2022 | Giacobini | A61K 31/7105 |

FOREIGN PATENT DOCUMENTS

| | | |
|---|---|---|
| EP | 3378378 A1 | 9/2018 |
| WO | 2019202114 A1 | 10/2019 |

OTHER PUBLICATIONS

Jason Gardosi, "Customized Fetal Growth Standards: Rationale and Clinical Application," Seminars in Perinatology, vol. 28, No. 1, Feb. 2004, pp. 33-40.
Extended European Search Report for European Patent Application No. 21 817 805.1 dated May 27, 2024, pp. 1-11.
International Search Report for International Application No. PCT/SG2021/050305 dated Sep. 1, 2021, pp. 1-4.
Written Opinion of the International Searching Authority for International Application No. PCT/SG2021/050305 dated Sep. 1, 2021, pp. 1-6.
Office Action for Chinese Patent Application No. 2021800402633 dated Jun. 26, 2025, pp. 1-6.
Office Action for Chinese Patent Application No. 2021800402633 dated Jan. 27, 2026, pp. 1-7.

* cited by examiner

FIG. 3 determine measurements of a
baby bump over a time period

302

Point 1
$(x_1, y_1)$

Point 2
$(x_2, y_2)$

Point 1
$(x_1, y_1)$

Point 2
$(x_2, y_2)$

Point 1

Point 2

Curved
Distance

Z Axis

X Axis

Y Axis

SYSTEM OF MONITORING FOETAL GROWTH, METHODS OF MONITORING AND FORMING THE SYSTEM

CROSS-REFERENCE TO RELATED APPLICATION

This application claims the benefit of priority of Singapore application No. 10202005227W filed Jun. 3, 2020, the contents of it being hereby incorporated by reference in its entirety for all purposes.

TECHNICAL FIELD

Various embodiments of this disclosure may relate to a system for monitoring foetal growth. Various embodiments of this disclosure may relate to a method of forming a system for monitoring foetal growth. Various embodiments of this disclosure may relate to a method of monitoring foetal growth.

BACKGROUND

Two of the most common practices in estimating foetal size are ultrasound imaging measurement and fundal height measurement by tape. Ultrasound sizing is the golden standard and has relatively satisfactory accuracy. Currently, a typical woman in healthy pregnancy goes for three ultrasound tests to monitor pregnancy. The first one is usually scheduled late in the first trimester, around the 11 to 14-week mark, the second ultrasound comes around the 18 to 20-week mark, and the third one is around the 32 to 34-week mark. The complexity and costs of ultrasound tests prevent them to be performed more often. It may be impractical for every pregnant woman to go for ultrasound test every week just to know how a healthy foetus is growing.

Fundal Height is one of the most useful and economical parameters used in clinical practice in estimating foetal size between 18 to 32 weeks. It is defined as the size of the uterus and is measured from the top of the uterus to the top of the pubic symphysis. The current common practice is to use a tape measure to run along the belly and plot it in a chart against gestational age and/or compare it with an internationally standardised chart (INTERGROWTH-21st). Despite its simplicity, it is difficult for this measurement to be done accurately by the pregnant woman herself. Doctors and midwives also need training before being able to perform this measurement accurately. Other than difficulties in performing the measurement, the usefulness of the data is also diminished by practicality issues. The horizontal comparison amongst other pregnant women is biased as differences in ethnicity, body measurements, and nutrition all play important roles in estimating health in the growth. A standard chart for all women is not accurate enough for certain races and ethnicity. Wrong estimations and comparisons may cause anxiety in some cases, or false security in other cases. A longitudinal chart of one's own measurements has the advantage of having an inherent baseline. However, limitations in medical resources may prohibit the measurements to be done frequently enough. Ideally, the interval between two measurements should be within one to two weeks, but women normally only go for prenatal check-up once per month. In poorer or more remote regions, the frequency may even be lower. This lack of monitoring may prevent serious foetal health problems from being detected early. In summary, although foetal growth estimation, especially its progression within pregnancy, is essential in monitoring foetal health, its practical difficulties prohibit its frequent administration at home, thus hampering its usefulness.

SUMMARY

Various embodiments may relate to a system for monitoring foetal growth. The system may include a plurality of devices. Each device of the plurality of devices may be configured to determine measurements of a baby bump over a time period, and may be further configured to store the measurements. The system may also include a server configured to receive the measurements from each of the plurality of devices. The server may be configured to compare the measurements from different devices of the plurality of devices. The system or server may be further configured to send an alert upon detecting an abnormality based on the measurements from the different devices of the plurality of devices.

Various embodiments may relate to a method of forming a system for monitoring foetal growth. The method may include providing a plurality of devices. Each device of the plurality of devices may be configured to determine measurements of a baby bump over a time period, and may be further configured to store the measurements. The method may also include providing a server configured to receive the measurements from each of the plurality of devices. The server may be configured to compare the measurements from different devices of the plurality of devices. The system or server may be further configured to send an alert upon detecting an abnormality based on the measurements from the different devices of the plurality of devices.

Various embodiments may relate to a method of monitoring foetal growth. The method may include determining measurements of a baby bump over a time period using each device of a plurality of devices, each device of the plurality of devices configured to store the measurements. The measurements from each device of the plurality of devices may be received by a server. The server may be configured to compare the measurements from different devices of the plurality of devices. The system or server may be further configured to send an alert upon detecting an abnormality based on the measurements from the different devices of the plurality of devices.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

FIG. 3 shows a general illustration of a method of monitoring foetal growth according to various embodiments.

DESCRIPTION

The following detailed description refers to the accompanying drawings that show, by way of illustration, specific details and embodiments in which the invention may be practised. These embodiments are described in sufficient detail to enable those skilled in the art to practise the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

Embodiments described in the context of one of the systems or methods are analogously valid for the other systems or methods. Similarly, embodiments described in the context of a method are analogously valid for a system, and vice versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the context of various embodiments, the articles "a", "an" and "the" as used with regard to a feature or element include a reference to one or more of the features or elements.

In the context of various embodiments, the term "about" or "approximately" as applied to a numeric value encompasses the exact value and a reasonable variance.

As used herein, the term "and/or" includes any and all combinations of one or more of the associated listed items.

Various embodiments may seek the address the various issues faced by conventional ways of monitoring foetal health. Various embodiments may have advantages over conventional ways of monitoring foetal health.

Figure 1:
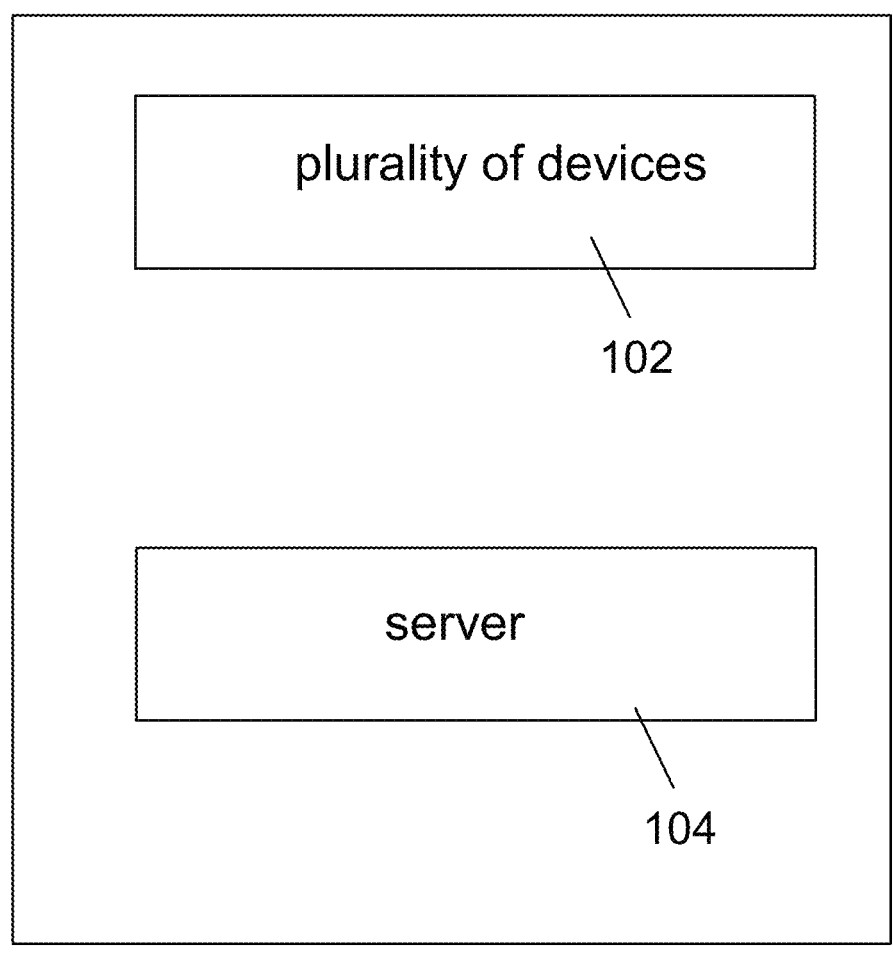
FIG. 1 shows a general illustration of a system for monitoring foetal growth according to various embodiments.

FIG. 1 shows a general illustration of a system for monitoring foetal growth according to various embodiments. The system may include a plurality of devices 102 (also referred to as baby bump measurement and recording devices). Each device of the plurality of devices 102 may be configured to determine measurements of a baby bump over a time period, and may be further configured to store the measurements. The system may also include a server 104 configured to receive the measurements from each of the plurality of devices 102. The server 104 may be configured to compare the measurements from different devices of the plurality of devices 102. The server 104 or the system may be further configured to send an alert upon detecting an abnormality based on the measurements from the different devices of the plurality of devices 102.

In other words, the system may include a plurality of devices 102 and a server 104 in communication with the plurality of devices 102. Each of the plurality of devices 102 may be configured to take or determine measurements of a baby bump of a pregnant mother or woman over a period of time. Each device may also store the measurements taken over the period. Additionally, the server 104 may be configured to detect any abnormality by comparing the measurements across different devices of the plurality of devices 102.

In various embodiments, measurements of a baby bump may refer to measurements indicating a size of the baby bump. The measurements may be length measurements. For instance, the measurements may refer to a distance or length between two spots of the baby bump, such as a highest point of an uterus of the pregnant mother or woman and a highest point of a pubic symphysis of the pregnant mother or woman. The distance or length between the highest point of the uterus and the highest point of the pubic symphysis may be referred to as a fundal height, and may be indicative of the size of the baby bump.

In various embodiments, each device of the plurality of devices 102 may include one or more sensors used in the determination of the measurements. The one or more sensors are selected from a group consisting of optical sensors, motion sensors, and ranging apparatuses. Examples of optical sensors may include red-green-blue (RGB) cameras, infrared (IR) cameras, or time-of-flight (TOF) cameras. Examples of motion sensors may include accelerometers or gyroscopes. Examples of ranging apparatuses may include light detection and ranging (LiDAR) sensors, or dot projectors.

In various embodiments, the one or more sensors may be configured to capture one or more images of the baby bump. The one or more images may be still images or frames from a video. Measurements of the baby bump may be determined or taken from the one or more images. In various other embodiments, measurements of the baby bump may be directly taken. For instance, in LiDAR, laser beams may be emitted from the device towards the baby bump. The laser beams may be reflected by the baby bump towards the device. The time taken for a laser beam to travel from the device to the baby bump and the time taken for the reflected laser beam to travel from the baby bump back to the device may be measured to determine the distance of the device from the baby bump. By targeting two spots of the baby bump and measuring the lengths or distances between each spot and the device, the length or distance between the two spots, e.g. a highest point of an uterus of the pregnant mother or woman and a highest point of a pubic symphysis of the pregnant mother or woman, may be determined.

In various embodiments, the length or distance may be a curved length or curved distance between the two spots or points (also referred to as end points). In various embodiments, the device may include a suitable software to determine or measure the curved length or curved distance. The device or software may be configured to generate or include a plurality of discrete points between the two points (also referred to as end points). The plurality of discrete points may be generated along a curved line (e.g. when the baby bump is oriented such that two end points are at the side when viewed from the device) or a straight line (e.g. when the baby bump is oriented such that the two end points are visible in front of the device). The software may be configured to generate a point cloud representing a curved surface of the baby bump based on the plurality of discrete points. The device or software may be configured to fit a three-dimensional curve such as a B-spline curve to points along a curved line defining the curved surface in the point cloud. In other words, the device or software may generate a suitable three dimensional curve, e.g. a B-spline curve, based on the plurality of discrete points. The fitted three-dimensional curve may include a plurality of interpolated points. The device or software may be further configured to calculate or determine a length, which may be a straight length, between each pair of neighbouring interpolated points along the B-spline curve. The curved distance or length (between the two end points) may be a sum of all the lengths between the pairs of neighbouring interpolated points.

In various embodiments, each device of the plurality of devices 102 may further include a memory storage configured to store the measurements. The memory storage may, for instance, be random access memory, magnetic storage memory, or phase change random access memory.

In various embodiments, each device of the plurality of devices 102 may further include a telecommunication module, e.g. a transmitter or a transceiver, configured to transmit the measurements to the server 104.

In various embodiments, each device of the plurality of devices 102 may further include a display for displaying information regarding the measurements. The display may show a graphics user interface for the user, i.e. the pregnant mother or woman, to control the information to be displayed.

In various embodiments, the server may be configured to compare the measurements of a predetermined group of pregnant mothers or women that is selected from one or more parameters. For instance, the one or more parameters may include ethnicity, age, body height, body weight, gestational age and country of residence. The progress of the size of baby bumps may vary amongst pregnant mothers or women of different ethnicities, ages, body sizes etc. As such, it may be more accurate to make comparisons between pregnant mothers or women of similar profiles. This in turn may be more effective in preventing anxiety in some cases, or false security in other cases.

In various embodiments, the abnormality of the baby bump may refer to any deviation from a predetermined range regarding the progress of the size of the baby bump. The predetermined range may be based on measurements of different pregnant mothers or women of the predetermined group. Measurements of a particular pregnant mother or woman may be compared against a database stored on the server 104. The database may be constructed based on measurements of other pregnant mothers or women. In various embodiments, the measurements of the particular pregnant mother or woman may be added to the database, and the database may be continuously be refreshed or modified as measurements of more pregnant mothers or women are added to the database. In various other embodiments, the database may be constructed based on preset measurements, and may not be modified.

In various embodiments, the system or the server 104 may be further configured to send the alert upon detecting the abnormality by comparing measurements determined by a device of the plurality of devices at different times during the time period. In other words, an alert may be provided when an abnormality, i.e. a deviation from a predetermined range, arises when measurements of a specific device are compared with previous measurements (determined previously and relating to the same pregnant mother or woman) of the specific device. For instance, if the measurements indicate no growth in the foetal size as compared to previous measurements taken a month ago (when a growth of e.g. 2 cm-5 cm is expected), an alert may be provided. The comparison between the measurements at different times may be carried out by the specific device or the server 104. The specific device or the server 104 may then send the alert upon detecting the abnormality.

In various embodiments, the system or the server 104 may be further configured to send the alert upon detecting the abnormality by comparing the measurements from each device with clinical data stored in the server. The clinical data, e.g. sonographic results, may be obtained from clinical trials and may be stored in the server 104. Clinical trials may provide a a medical grade data model as a reference for the measurements to be compared with. When measurements from a device is received, the server 104 may compare the measurements with the clinical data stored in the server. In various embodiments, the server 104 may be configured to compare the measurements with clinical data of a predetermined group of pregnant mothers or women that is selected from one or more parameters, e.g. height, weight, ethnicity, country of residence. For instance, measurements of a Chinese Singaporean woman of height 160 cm and weight 50 kg may be compared with clinical data of other Chinese Singaporean women of heights 155 cm-165 cm and weights 45 kg-55 kg that is stored in the server 104.

In various embodiments, the system or the server 104, may be configured to send the alert regarding the abnormality of the baby bump of a pregnant mother to communication devices of one or more preassigned contacts of the pregnant mother. The one or more preassigned contacts may, for instance, include a family physician or doctor, a gynaecologist, a nurse, or any other medical professional of the pregnant mother or woman. The one or more preassigned contact may additionally or alternatively include the pregnant mother or woman herself, and/or one or more family members of the pregnant mother or woman. The alert may, for instance, be sent in the form of short message service (SMS) messages or voice messages to the phones of the preassigned contacts, or in the form of email messages to the email addresses of the preassigned contacts accessed by a suitable computer or computing device of the preassigned contacts. In various embodiments, the alert provided when an abnormality is detected from previous measurements from the pregnant mother may be different compared to an abnormality detected by comparing measurements of the plurality of devices of different mothers. For instance, the SMS or email messages sent may be worded differently. Likewise, the alert provided when an abnormality is detected by comparing measurements with the clinical data stored in the server 104, may be different compared to an abnormality detected by comparing measurements of the plurality of devices of different mothers.

In various embodiments, each device of the devices may be a smartphone, a tablet, or a smart watch.

In various embodiments, the measurements may be transmitted from the plurality of devices 102 to the server 104 in the form of signals. The signals may include data indicating the measurements. The signals may be transmitted from the plurality of devices 102 to the server 104 via wireless means. The signals may, for instance, be in the form of cellular signals such as third generation (3G) signals or fourth generation (4G) signals, WIFI signals, or Bluetooth signals. In various embodiments, the measurements may be transmitted from the plurality of devices 102 to the server using a combination of different signals. For instance, a smart watch may take the measurements, and the measurements may be transmitted to a paired smart phone via WIFI signals or Bluetooth signals. Upon receiving the measurements, the smart phone may transmit the measurements to the server 104 via 3G or 4G signals.

Figure 2:
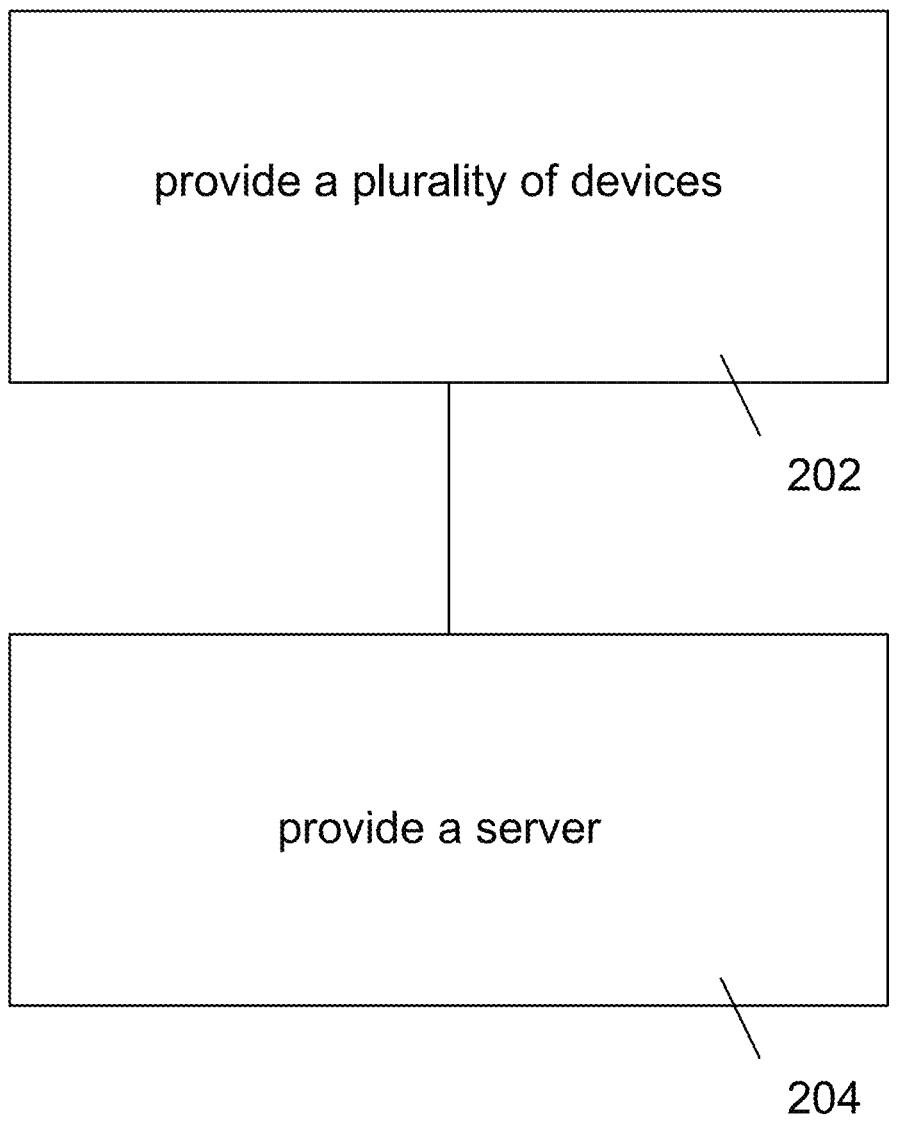
FIG. 2 shows a general illustration of a method of forming a system for monitoring foetal growth according to various embodiments.

FIG. 2 shows a general illustration of a method of forming a system for monitoring foetal growth according to various embodiments. The method may include, in 202, providing a plurality of devices. Each device of the plurality of devices may be configured to determine measurements of a baby bump over a time period, and may be further configured to store the measurements. The method may also include, in 204, providing a server configured to receive the measurements from each of the plurality of devices. The system or the server may be configured to compare the measurements from different devices of the plurality of devices. The server may be further configured to send an alert upon detecting an abnormality based on the measurements from the different devices of the plurality of devices.

In other words, the method may include providing a plurality of devices to determine and store measurements of foetal growth, and providing a server to receive and process the measurements.

In various embodiments, each device of the plurality of devices may include one or more sensors used in the determination of the measurements.

In various embodiments, the one or more sensors may be selected from a group consisting of optical sensors, motion sensors, and ranging apparatuses.

In various embodiments, the measurements determined by each device of the plurality of devices may relate to a fundal height of the baby bump.

In various embodiments, each device of the plurality of devices may further include a memory storage configured to store the measurements. Each device of the plurality of devices may further include a telecommunication module configured to transmit the measurements to the server. Each device of the plurality of devices may further include a display for displaying information regarding the measurements.

In various embodiments, the server may be configured to compare the measurements of a predetermined group of pregnant mothers or women that is selected from one or more parameters. For instance, the one or more parameters may include ethnicity, age, body height, body weight, gestational age and country of residence.

In various embodiments, the system or the server may be configured to send the alert regarding the abnormality of the baby bump of a pregnant mother or woman to communication devices of one or more preassigned contacts of the pregnant mother or woman.

In various embodiments, each device of the devices may be a smartphone, a tablet, or a smart watch.

In various embodiments, the system or the server may be further configured to send the alert upon detecting the abnormality by comparing measurements determined by a device of the plurality of devices at different times during the time period.

In various embodiments, the system or the server may be further configured to send the alert upon detecting the abnormality by comparing the measurements from each device with clinical data stored in the server.

Figure 3:
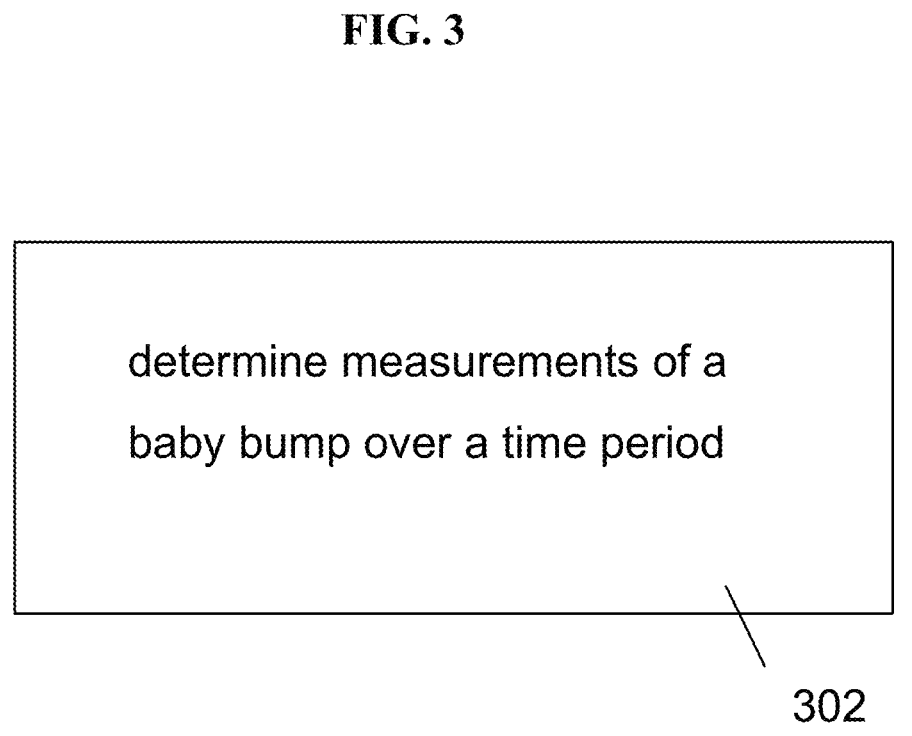

FIG. 3 shows a general illustration of a method of monitoring foetal growth according to various embodiments. The method may include, in 302, determining measurements of a baby bump over a time period using each device of a plurality of devices, each device of the plurality of devices configured to store the measurements. The measurements from each device of the plurality of devices may be received by a server. The server may be configured to compare the measurements from different devices of the plurality of devices. The system or the server may be further configured to send an alert upon detecting an abnormality based on the measurements from the different devices of the plurality of devices.

In various embodiments, determining measurements of the baby bump may include determining measurements of a fundal height of the baby bump. The measurements of the baby bump may be based on a distance or length between two points of the baby bump of a pregnant mother or woman. For instance, the two points may be a point of an uterus of the pregnant mother or woman, and a point of a pubic symphysis of the pregnant mother or woman. In various embodiments, the method may further include positioning a reference object before determining the measurements. The reference object may be a household object such as a coin. The reference object may be positioned on the baby bump, i.e. the belly of the pregnant mother or woman. The reference object may provide a reference when determining measurements of the baby bump.

In various embodiments, the distance or length may be a curved distance or curved length between the two points.

In various embodiments, each device of the plurality of devices may include one or more sensors used in the determination of the measurements. The one or more sensors may be selected from a group consisting of optical sensors, motion sensors, and ranging apparatuses. The one or more sensors may be selected from a group consisting of red-green-blue (RGB) cameras, infrared (IR) cameras, time-of-flight (TOF) cameras, accelerometers, gyroscopes, light detection and ranging (LiDAR) sensors, and dot projectors.

In various embodiments, the system or the server may be further configured to send the alert upon detecting the abnormality by comparing measurements determined by a device of the plurality of devices at different times during the time period.

In various embodiments, the system or the server may be further configured to send the alert upon detecting the abnormality by comparing the measurements from each device with clinical data stored in the server.

Various embodiments may try to solve or address pain points in foetal size estimation and monitoring. Various embodiments may involve the steps of measure, chart, compare and alert. Image-, video- and/or motion-based measurements may be carried out to ensure that the measurements can be accurately performed by the mother or an untrained person at home (measure). Frequent measurements may be recorded to obtain a personalised foetal growth progression (chart). In addition, curated comparison across mothers of similar conditions and situations may be done to eliminate biases in standardised charts (compare). Further, any longitudinal or horizontal abnormalities in the growth may be automatically reported to the user's assigned contacts such as family members and physicians (alert).

Measure

The front end of the platform is the baby bump measurement and recording device. The device may include one/multiple optical sensors (including but not limited to RGB cameras, IR cameras and TOF cameras), motion sensors (including but not limited to accelerometers and gyroscopes), or ranging apparatus (including but not limited to LiDAR sensors and dot projectors), a display, memory storage and a telecommunication module (including but not limited to modules capable of operating cellular network, WIFI, Bluetooth signals). One example of such devices may be a modern smartphone (e.g. iPhone 6s). The device may have the software to perform the measurement in the following steps.

Under Step 1, the mother's entire belly and a reference object (e.g. a common household object such as a coin) may be positioned within the viewfinder in a well-lit environment according to guiding overlays in the viewfinder. The reference object may only be used when absolute distance measurement cannot be achieved.

Under Step 2, based on the result, the user may or may not need to move the device according to instructions on screen to capture the belly from different perspectives.

Under Step 3, the software may identify the baby bump curve from the image(s), may assign physical scales based on the object in the picture and/or data from the motion and ranging sensors, and may calculate the physical measurement of the baby bump.

Under Step 4, the software may show the measurement on the display and may record it.

Light Detection and Ranging (LiDAR) is a method to determine distance between a target and the detector. This may be done by emitting light (laser) and measuring the time taken for light to be reflected back to the receiver. With the advances of LiDAR cameras, absolute distance measurement may be taken without a reference object (e.g. a coin).

The LiDAR camera may be an optical imagining instrument that not only captures the colour image of a field of view (FOV), but also the depth image. The colour image may be made up of pixels which include colour (RGB) information. Depth images are like colours images, except each pixel represents the distance between the camera and the object/target in the FOV.

Figure 4A:
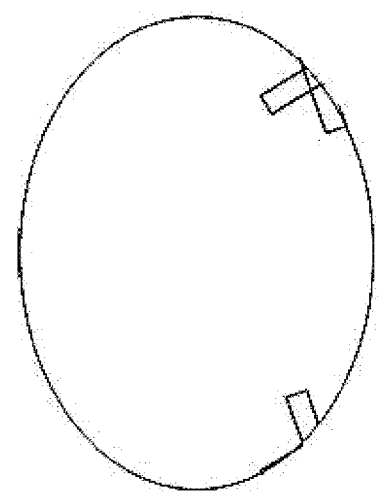
FIG. 4A shows a schematic of a water melon according to various embodiments.
Figure 4B:
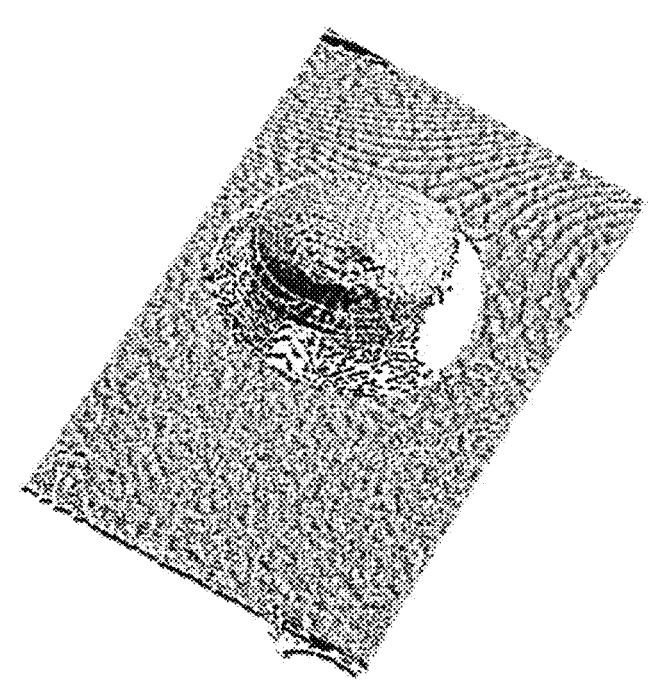
FIG. 4B shows a point cloud of the water melon according to various embodiments.

With the colour images and depth images, a point cloud can be computed. A point cloud may refer to a set of data points in 3D space. A single point represents the positional coordinates x, y, z. FIG. 4A shows a schematic of a water melon according to various embodiments. FIG. 4B shows a point cloud of the water melon according to various embodiments.

Figure 5A:
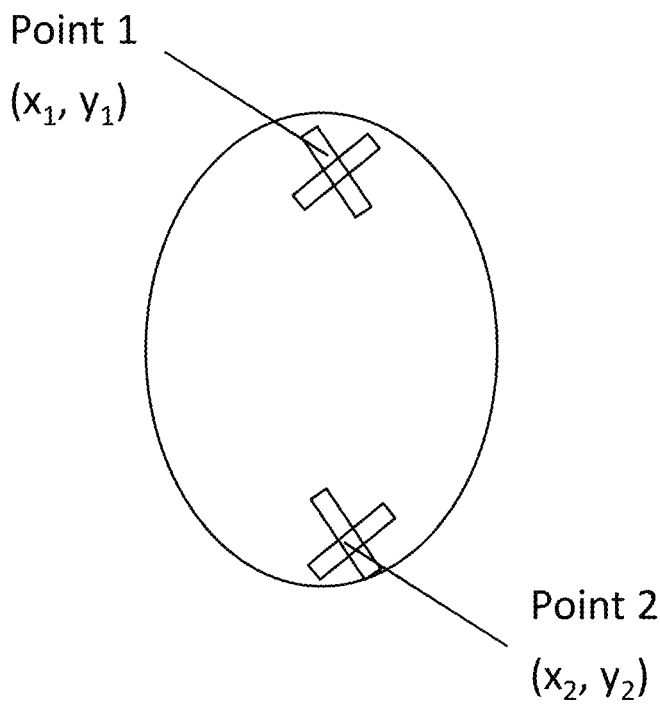
FIG. 5A shows a schematic of the watermelon oriented such that the starting point and ending point are at the front according to various embodiments.
Figure 5B:
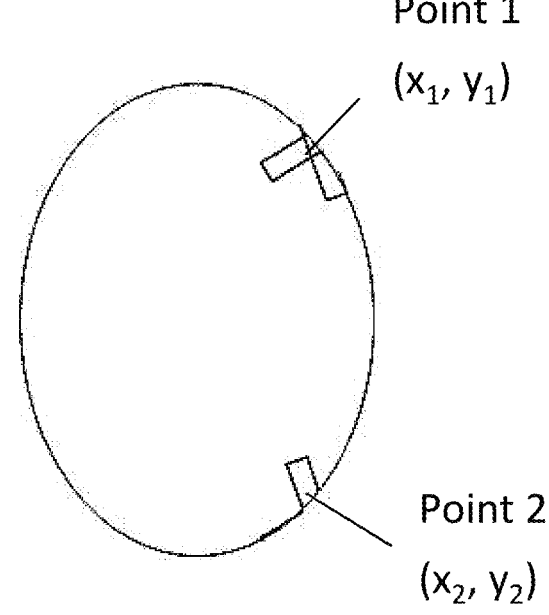
FIG. 5B shows a schematic of the watermelon oriented such that the starting point and ending point at the side according to various embodiments.

In order to find the distance or length between two point within the FOV, two point (pixels) is selected from the colour image (represented by schematics) as shown in the figures below. FIG. 5A shows a schematic of the watermelon oriented such that the starting point and ending point are at the front according to various embodiments. FIG. 5B shows a schematic of the watermelon oriented such that the starting point and ending point at the side according to various embodiments.

A colour image data may be saved in a two-dimensional array format depending on the camera's horizontal and vertical pixel format. Each selected point on the colour image has its own array location information (e.g. row & column).

Figure 5C:
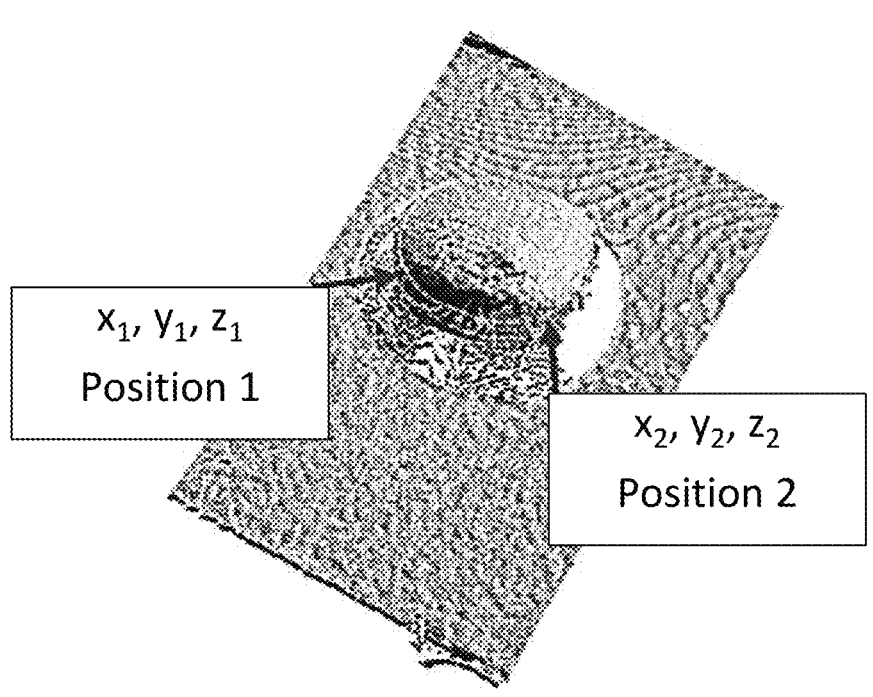
FIG. 5C shows a point cloud with information on the two points according to various embodiments.

A point cloud data may be saved in a 3 different 2D arrays (x array, y array, z array) The array location of the selected pixels from the colour image may correspond to the sample location in the point cloud. FIG. 5C shows a point cloud with information on the two points according to various embodiments. Thus position 1 and position 2 may be known as shown in FIG. 5C.

Figure 6A:
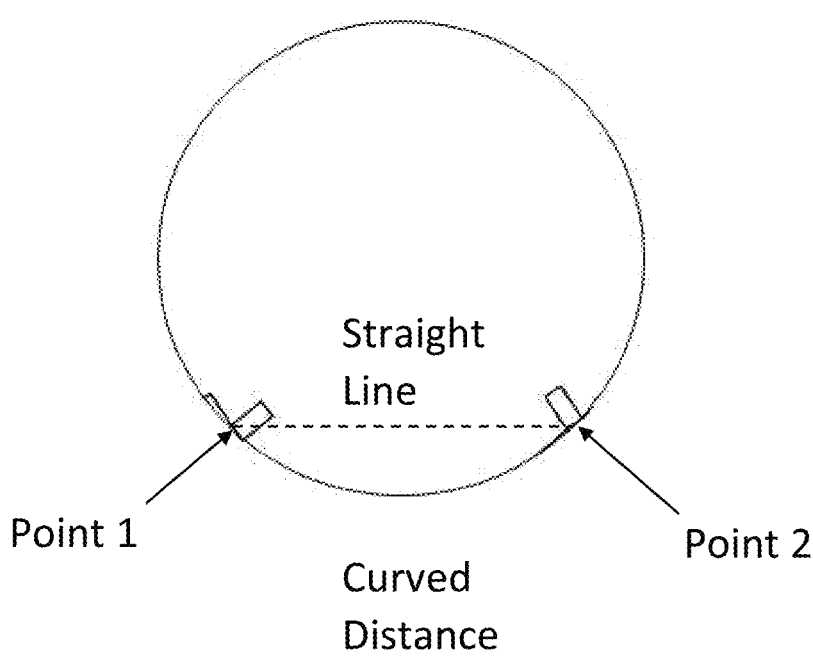
FIG. 6A is a schematic illustrating the measurement of the fundal height using light detection and ranging (LiDAR) according to various embodiments.
Figure 6B:
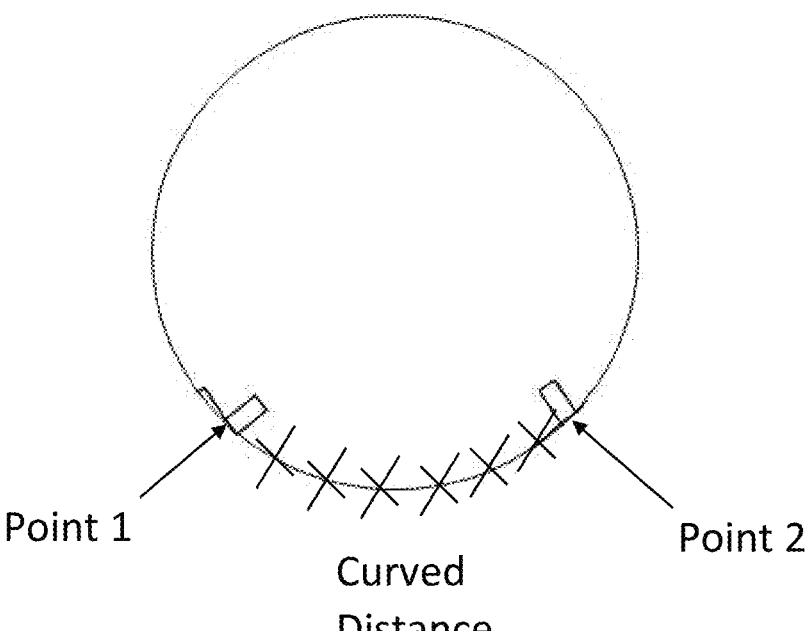
FIG. 6B shows the measurement of the curved distance or curved length between Point 1 and Point 2 according to various embodiments.
Figure 6C:
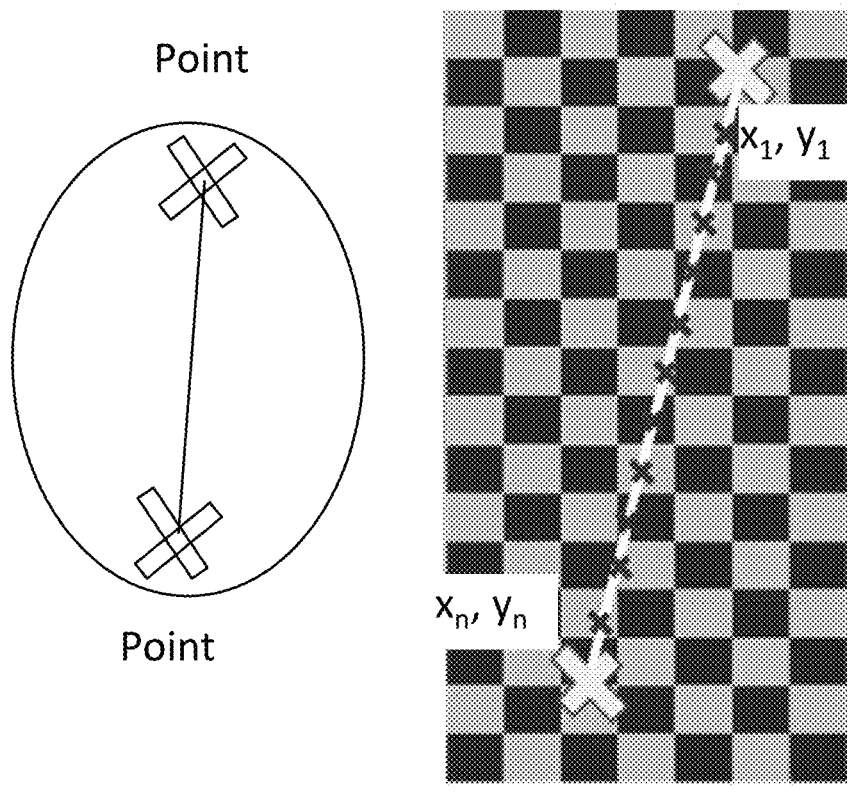
FIG. 6C shows (left) a schematic of a curved sample having two end points at the front of the curved sample according to various embodiments; and (right) determination of the discrete points or pixels that fall between the two end points according to various embodiments.

FIG. 6A is a schematic illustrating the measurement of the fundal height using light detection and ranging (LiDAR) according to various embodiments. The curved distance or curved length may need to be measured as shown in FIG. 6A. FIG. 6B shows the measurement of the curved distance or curved length between Point 1 and Point 2 according to various embodiments. In order to measure the curved distance, multiple discrete points may be identified between Point 1 and Point 2 along the curve. FIG. 6C shows (left) a schematic of a curved sample having two end points at the front of the curved sample according to various embodiments; and (right) determination of the discrete points or pixels that fall between the two end points according to various embodiments. With the two end points on the front view of the curved sample, the points or pixels that fall in between the two end points may be identified or calculated with the linear equation: y=mx+c.

Figure 6D:
FIG. 6D is a three-dimensional plot showing the construction of the curved line according to various embodiments.

With these colour image pixel locations, the positional coordinates may be extracted from the point cloud to construct the point cloud of the surface of the curved sample as shown in FIG. 6D. FIG. 6D is a three-dimensional plot showing the construction of points along the curved line according to various embodiments. The curved line defines the surface of the curved sample.

Figure 6E:
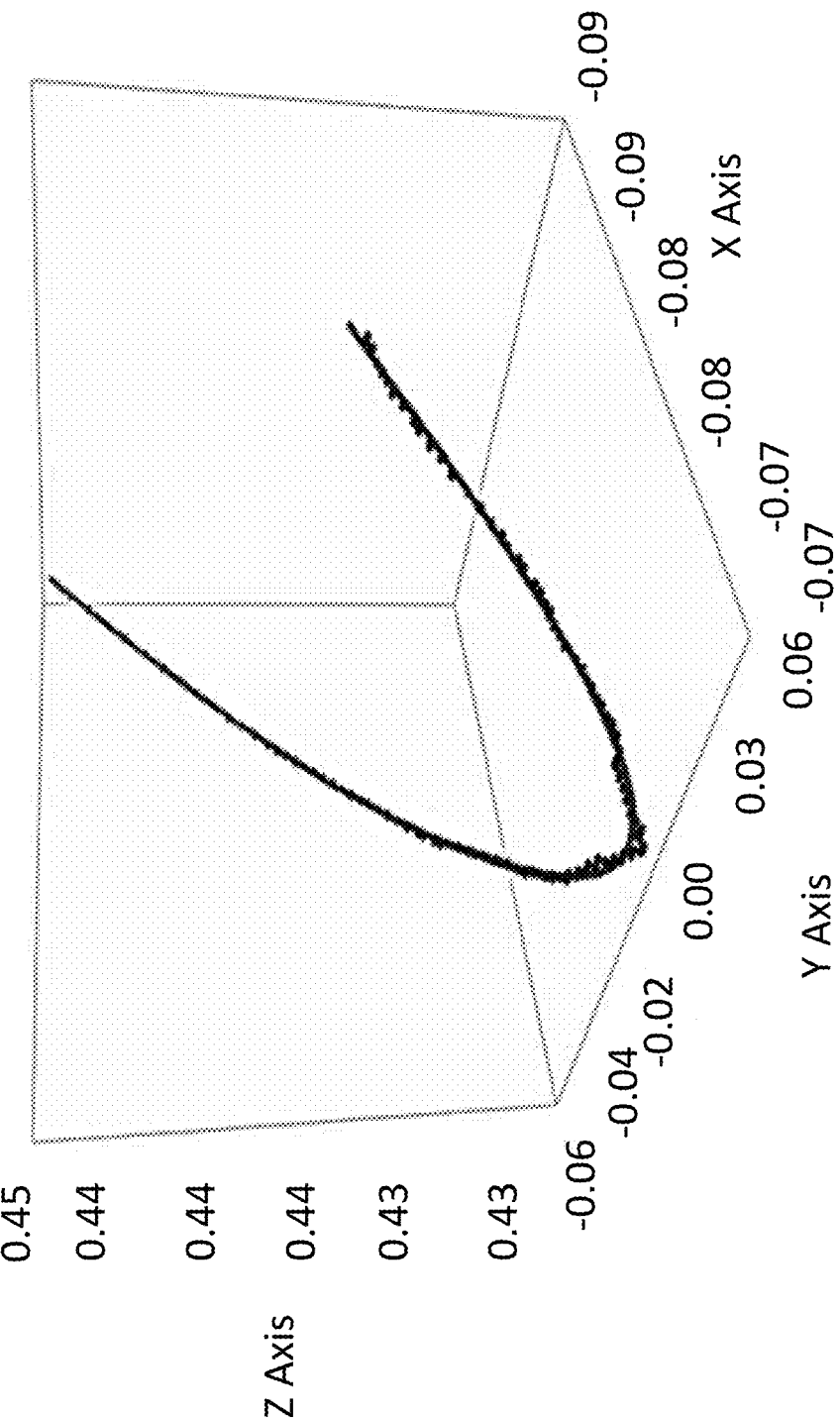
FIG. 6E is a three-dimensional plot showing the fitting of a B-spline line onto the curved line generated in FIG. 6D according to various embodiments.

A three-dimensional curve, e.g. a B-spline curve, may then be fitted into the points of the curved line as shown in FIG. 6E. below. FIG. 6E is a three-dimensional plot showing the fitting of a B-spline line onto the curved line generated in FIG. 6D according to various embodiments. Spline interpolation may fit a polynomial over each interval in the data and may output 500 interpolated points.

The sum of the lengths between neighbouring interpolated points may be calculated to compute the curved distance or curved length. The straight line lengths or distances between each pair of neighbouring interpolated points may be calculated as follows:

$$\text{Distance}_1 = \sqrt{(x_2 - x_1)^2 + (y_2 - y_1)^2 + (z_2 - z_1)^2}$$

$$\cdots$$

$$\text{Distance}_n = \sqrt{(x_{n-1} - x_n)^2 + (y_{n-1} - y_n)^2 + (z_{n-1} - z_n)^2}$$

$$\text{Curved distance} = \text{Sum} \left(\text{Distance}_1 : \text{Distance}_n\right)$$

Chart

The device may maintain a local record of all the baby bump measurements and the changes between any two consecutive measurements with different time stamps. The device or software may also provide a chart showing user-selected measurements and changes along the time axis upon user's, i.e. pregnant mother or woman's, request.

The device or software may also use machine learning on the user's data to assess the health of growth of the foetus. The device or software may then show the assessment based on the user's progress.

Compare

The fundal height measurements of all the users, i.e. pregnant mothers or women, with time stamps together with some basic biodata (including but not limited to age, height, weight, gestational age, country of residence) may be uploaded to a remote central database upon users' acceptance. The database may store this data and may analyse the data to provide insights and/or improve its measurement, assessment and prediction algorithms.

Each individual user may be able to request a report on her percentile based on various criteria input from the user.

Alert

Based on the self-calibrated growth curve and vast amount of data collected from women in similar environment and circumstances, an algorithm from the server end may detect abnormalities in the foetal growth and may push alerts to the device and user-assigned contacts such as her family members or her physician.

Various embodiments may relate to a platform capable of measuring, recording and analysing baby bumps using one or multiple cameras with or without motion sensors in a single device. The device may capture a short video clip or a picture of the pregnant belly. The computer vision algorithm may analyse the video or the picture to obtain measurement of the baby bump. The algorithm may also corroborate with data from motion sensors such as accelerometers and/or gyroscopes to improve accuracy. The system may record all the baby bump measurements at regular intervals and may submit them to a remote database. The remote database may be able to make an assessment on the growth of the foetus by analysing data from the mass of users. Each individual user may also be able to see a progression of growth along her own gestation and to compare her progress with other users in the database. If the growth is abnormal, the system may alert the user and help to provide a record to the user's physician.

Various embodiments may involve motion- and vision-based baby bump measurements. Various embodiments may have the advantage of longitudinal foetal growth progression record with personalised baseline. Various embodiments may include horizontal assessment of foetal health with considerations on multiple contributing factors. Various embodiments may relate to artificial intelligence based assessment of foetal growth based from longitudinal and horizontal data.

Various embodiments may relate to a database and longitudinal monitoring of foetal growth. A database (which may be referred to as a correlation database) may be built or established between the baby bump measurements and the sonographic results obtained through a clinical trial. Various embodiments may include a server, e.g. a cloud server, that collects, stores, and analyses the data including the measurements taken from the plurality of devices. The database may use multi-modal artificial intelligence (AI) to evaluate if there is risk to the foetal development based on a medical grade data model that the system generates using data (including corroboration with sonographic results) from clinical trials and optimised using vast amount of user data (from the plurality of devices). The backbone of the data model may be the user's own baseline (history of the longitudinal measurement results). Multiple other factors (e.g. height, weight, ethnicity, country of residence etc.) may be fed into the data model to correct for individual and cohort differences. A gradual and stable increase of the baby bump measurements may be monitored along weekly measurements. If the increase in baby bump is out of the expected curve, a warning message may be sent to the user.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. A system for monitoring foetal growth, the system comprising:

a plurality of devices, each device of the plurality of devices configured to determine measurements of a baby bump over a time period, and further configured to store the measurements, wherein the measurements are determined by light detection and ranging technology; and a server configured to receive the measurements from each of the plurality of devices;

wherein the server is configured to compare the measurements from different devices of the plurality of devices; and wherein the system is further configured to send an alert upon detecting an abnormality based on the measurements from the different devices of the plurality of devices.

2. The system according to claim 1, wherein each device of the plurality of devices comprises one or more sensors used in the determination of the measurements and the one or more sensors are selected from a group consisting of optical sensors, motion sensors, and ranging apparatuses.

3. The system according to claim 1, wherein the measurements determined by each device of the plurality of devices relates to a fundal height of the baby bump.

4. The system according to claim 1, wherein each device of the plurality of devices further comprises a memory storage configured to store the measurements.

5. The system according to claim 1, wherein each device of the plurality of devices further comprises a display for displaying information regarding the measurements.

6. The system according to claim 1, wherein the server is configured to compare the measurements of a predetermined group of pregnant mothers that is selected from one or more parameters.

7. The system according to claim 6, wherein the one or more parameters comprise ethnicity, age, body height, body weight, gestational age and country of residence.

8. The system according to claim 1, wherein the system is configured to send the alert regarding the abnormality of the baby bump of a pregnant mother to communication devices of one or more preassigned contacts of the pregnant mother.

9. The system according to claim 1, wherein each device of the devices is a smartphone, a tablet, or a smart watch.

10. The system according to claim 1, wherein the system is further configured to send the alert upon detecting the abnormality by comparing measurements determined by a device of the plurality of devices at different times during the time period.

11. The system according to claim 1, wherein the system is further configured to send the alert upon detecting the abnormality by comparing the measurements from each device with clinical data stored in the server.

12. The system according to claim 1, wherein the measurements of the baby bump are based on a distance between two points of the baby bump of a pregnant mother, wherein the plurality of devices are configured to:

generate a plurality of discrete points between the two points;

fit a three-dimensional curve to the plurality of discrete points, the three-dimensional curve including a plurality of interpolated points;

determine a length between each pair of neighbouring interpolated points; and sum all the lengths between the pairs of neighbouring interpolated points to be a length between the two points.

13. The system according to claim 12, wherein the plurality of devices are further configured to:

prior to fitting a three-dimensional curve to the plurality of discrete points, generate a point cloud based on the plurality of discrete points; and fit a three-dimensional curve to the plurality of discrete points in the point cloud.

14. A method of forming a system for monitoring foetal growth, the method comprising:

providing a plurality of devices, each device of the plurality of devices configured to determine measurements of a baby bump over a time period, and further configured to store the measurements, wherein the measurements are determined by light detection and ranging technology; and providing a server configured to receive the measurements from each of the plurality of devices;

wherein the server is configured to compare the measurements from different devices of the plurality of devices; and sending an alert upon detecting an abnormality based on the measurements from the different devices of the plurality of devices.

15. A method of monitoring foetal growth, the method comprising:

determining measurements of a baby bump over a time period using each device of a plurality of devices, each device of the plurality of devices configured to store the measurements, wherein the measurements are determined by light detection and ranging technology;

receiving the measurements from each device of the plurality of devices by a server;

comparing, by the server, the measurements from different devices of the plurality of devices; and sending an alert upon detecting an abnormality based on the measurements from the different devices of the plurality of devices.

16. The method according to claim 15, wherein determining measurements of the baby bump comprises determining measurements of a fundal height of the baby bump.

17. The method according to claim 15, wherein the measurements of the baby bump are based on a distance between two points of the baby bump of a pregnant mother.

18. The method according to claim 17, wherein the two points are a point of a uterus of the pregnant mother and a point of a pubic symphysis of the pregnant mother, wherein the distance is a curved distance between the two points.

19. The method according to claim 15, further comprising:

sending the alert upon detecting the abnormality by comparing measurements determined by a device of the plurality of devices at different times during the time period.

20. The method according to claim 15, further comprising:

sending the alert upon detecting the abnormality by comparing the measurements from each device with clinical data stored in the server.

\* \* \* \* \*